United States Patent
Bakthavatchalam et al.

(10) Patent No.: US 7,323,478 B2
(45) Date of Patent: Jan. 29, 2008

(54) MELANIN CONCENTRATING HORMONE RECEPTOR LIGANDS

(75) Inventors: Rajagopal Bakthavatchalam, Madison, CT (US); Andrew Thurkauf, Ridgefield, CT (US); Alan Hutchison, Madison, CT (US)

(73) Assignee: Neurogen Corporation, Branford, CT (US)

( * ) Notice: Subject to any disclaimer, the term of this patent is extended or adjusted under 35 U.S.C. 154(b) by 677 days.

(21) Appl. No.: 10/820,344

(22) Filed: Apr. 8, 2004

(65) Prior Publication Data

US 2004/0229883 A1 Nov. 18, 2004

Related U.S. Application Data

(62) Division of application No. 10/385,973, filed on Mar. 11, 2003, now Pat. No. 6,753,336, which is a division of application No. 09/900,679, filed on Jul. 6, 2001, now Pat. No. 6,569,861.

(60) Provisional application No. 60/216,081, filed on Jul. 6, 2000.

(51) Int. Cl.
*A61K 31/445* (2006.01)

(52) U.S. Cl. ............ 514/317; 514/327; 514/331

(58) Field of Classification Search ............ 424/200, 424/200.1; 514/317, 327, 331
See application file for complete search history.

(56) References Cited

U.S. PATENT DOCUMENTS

| | | | |
|---|---|---|---|
| 3,845,058 A | 10/1974 | Lembo et al. | |
| 4,370,329 A | 1/1983 | Scherm et al. | |
| 4,370,330 A | 1/1983 | Scherm et al. | |
| 5,569,659 A | 10/1996 | Reitz | |
| 5,681,954 A | 10/1997 | Yamamoto et al. | |
| 5,859,246 A | 1/1999 | Thurkauf et al. | |
| 6,048,876 A | 4/2000 | Annoura et al. | |
| 6,057,371 A | 5/2000 | Glennon | |
| 6,172,229 B1 | 1/2001 | Thurkauf et al. | |
| 6,284,761 B1 | 9/2001 | Zhang et al. | |
| 6,753,336 B2 * | 6/2004 | Bakthavatchalam et al. | 514/317 |

FOREIGN PATENT DOCUMENTS

| | | |
|---|---|---|
| EP | 177392 | 9/1985 |
| EP | 188.887 | 5/1991 |
| EP | 390654 | 11/1994 |
| EP | 755923 | 1/1997 |
| EP | 624584 | 8/1998 |
| ES | 549465 | 3/1986 |
| JP | 2001-226269 | 8/2001 |
| WO | WO 96/14307 | 5/1996 |
| WO | WO 96/16040 | 5/1996 |
| WO | WO 97/41108 | 11/1997 |
| WO | WO 97/44334 | 11/1997 |
| WO | WO 98/03492 | 1/1998 |
| WO | WO 98/03493 | 1/1998 |
| WO | WO 98/03494 | 1/1998 |
| WO | WO 98/33784 | 8/1998 |
| WO | WO 99/19301 | 4/1999 |
| WO | WO 01/21169 | 3/2001 |
| WO | WO 01/21577 | 3/2001 |
| WO | WO 01/82925 | 11/2001 |
| WO | WO 01/87834 | 11/2001 |
| WO | WO 02/02744 | 1/2002 |
| WO | WO 02/06245 | 1/2002 |
| WO | WO 02/051809 | 7/2002 |

OTHER PUBLICATIONS

Kowalski et al., Therapeutic Potentila of Melanin-Concentrating Hormone-1 Receptor antagonists for the the treatment of Obesity; Expert Opinion Investig. Drugs (2004) 13(9): pp. 1113-1122.*

* cited by examiner

*Primary Examiner*—Johann Richter
*Assistant Examiner*—Ebenezer Sackey
(74) *Attorney, Agent, or Firm*—Ann T. Kadlecek; Seth A. Fidel

(57) ABSTRACT

Disclosed are compounds of the formula:

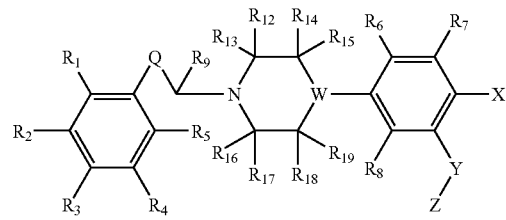

and the pharmaceutically acceptable salts thereof wherein Q, X, Y, Z, and $R_1$ $R_9$, and $R_{12}$-$R_{19}$ are defined herein.

These compounds are selective modulators of MCH 1 receptors that are, therefore, useful in the treatment of a variety of metabolic, feeding, and sexual disorders. Methods of treatment of such disorders and well as packaged pharmaceutical compositions are also disclosed.

15 Claims, No Drawings

MELANIN CONCENTRATING HORMONE RECEPTOR LIGANDS

CROSS-REFERENCE TO RELATED APPLICATIONS

This application is a divisional of U.S. patent application Ser. No. 10/385,973 filed Mar. 11, 2003, now U.S. Pat. No. 6,753,336, which is a divisional of U.S. patent application Ser. No. 09/900,679, filed Jul. 6, 2001, now U.S. Pat. No. 6,569,861, which claims priority to U.S. Provisional Application No. 60/216,081, filed Jul. 6, 2000.

BACKGROUND OF THE INVENTION

1. Field of the Invention

This invention relates to phenylcycloalkylmethylamino and phenylalkenylamino derivatives, including 1-phenyl-2-aminomethylcyclopropanes, that are modulators of melanin concentrating hormone type 1 (MCH 1) receptors. This invention also relates to pharmaceutical compositions comprising such compounds.

2. Description of the Related Art

Melanin concentrating hormone, or MCH, is a cyclic 19 amino acid neuropeptide that is produced within the hypothalamus of many vertebrate species including man. I.C.V. injection of MCH into the lateral ventricle of the hypothalamus has been shown to increase caloric consumption in rats over similarly treated control animals. Furthermore, rats having the ob/ob genotype exhibit a 50-80% increase in MCH mRNA expression as compared to leaner ob/+ genotype mice. MCH knockout mice are leaner than their MCH-producing siblings due to hypophagia and an increased metabolic rate. Thus, MCH is thought to be an important regulator of feeding behavior and body weight.

The MCH 1 receptor was originally obtained from human cDNA and genomic libraries and characterized as a 402 amino acid G-coupled protein receptor having substantial sequence identity to the somatostatin receptors. This receptor was named the SLC-1 receptor. A rat orthologue of the MCH 1 receptor was isolated from a rat brain cDNA library by Lakaye, et al. (BBA (1998) 1401: 216-220) and found to encode a 353 amino acid protein having seven transmembrane alpha helices and three consensus N-glycosylation sites. The rat MCH 1 receptor reported by Lakaye also disclosed was homologous to the human MCH 1 receptor disclosed earlier except for the removal of a 5' intron. Accordingly, Lakaye, et al., deduced the "corrected" amino acid sequence of the N-terminus of MCH 1 receptor is found within a sequence deposited for a 128 kb fragment of human chromosome 22 encompassing the earlier disclosed MCH 1 receptor gene (Genbank accession number: Z86090).

The earlier reported 402 amino acid MCH 1 receptor protein does not interact with MCH. Thus, the 353 amino acid receptor first reported by Lakaye, is now considered to be the correct full-length sequence for the human MCH 1 receptor.

Immunohistochemistry studies of rat brain sections indicate that the MCH 1 receptor is widely expressed in the brain. MCH 1 receptor expression was found in the olfactory tubercle, cerebral cortex, substantia nigra, basal forebrain CA1, CA2, and CA3 field of the hippocampus, amygdala, and in nuclei in the hypothalamus, thalamus, midbrain and hindbrain. Strong signals have been observed in the ventromedial and dorsomedial nuclei of the hypothalamus, two areas of the brain known to be involved in feeding behavior.

Upon binding MCH, MCH 1 receptors expressed in HEK 293 cell mediate a dose dependent release of intracellular calcium. Cells expressing MCH receptors have also been shown to exhibit a pertussis toxin sensitive dose-dependent inhibition of forskolin-elevated cyclic AMP, indicating that the receptor couples to a $G_{i/o}$ G-protein alpha subunit.

Because MCH has been shown to be an important regulator of food intake and energy balance, ligands capable of modulating the activity of the MCH 1 receptor are highly desirable for the treatment of eating disorders and metabolic disorders. Orally available, small molecule, non-peptide antagonists of the MCH 1 receptor are particularly sought for the treatment of obesity.

SUMMARY OF THE INVENTION

The invention provides novel compounds, particularly phenylcycloalkylmethylamino and phenylalkenylamino compounds, including 1-phenyl-2-aminomethylcyclopropanes, that are small molecule MCH receptor ligands, especially MCH 1 receptor ligands, that are non-peptide and amino acid free, which compounds exhibit a $K_i$ at the MCH receptor of less than 1 micromolar. Preferred MCH 1 receptors are mammalian receptors, including human and monkey MCH receptors and may either be cloned, recombinantly expressed receptors or naturally expressed receptors.

In certain embodiments these compounds also possess one or more, and preferably two or more, three or more, or all of the following properties in that they are: 1) multi-aryl in structure (having a plurality of un-fused or fused aryl groups), 2) orally available in vivo (such that a sub-lethal or pharmaceutically acceptable oral dose can provide a detectable in vivo effect such as a reduction of appetite), 3) capable of inhibiting the binding of MCH to the MCH receptor at nanonmolar concentrations or 4) capable of inhibiting the binding of MCH to the MCH receptor at sub-nanomolar concentrations.

The invention also provides novel compounds of Formula I, shown below, that bind specifically, and preferably with high affinity, to MCH receptors.

The invention also provides pharmaceutical compositions comprising compounds of Formula I together with at least one pharmaceutically acceptable carrier. The compounds are particularly useful in the treatment of metabolic, feeding, and sexual disorders. The invention further comprises a method of treating a patient in need of such treatment with a sufficient concentration of a compound of the invention. A preferred concentration is one sufficient to inhibit the binding of MCH to MCH 1 receptors in vitro. Treatment of humans, domesticated companion animals (pets) or livestock animals suffering such conditions with an effective amount of a compound of the invention is contemplated by the invention.

Also included in the invention are methods of treating eating disorders, particularly obesity and bulimia nervosa, comprising administering to a patient in need of such treatment a MCH 1 receptor modulator together with leptin, a leptin receptor agonist, or a melanocortin receptor 4 (MC4) agonist.

In a separate aspect, the invention provides methods of using compounds of this invention as positive controls in assays for receptor activity and using appropriately labeled compounds of the invention as probes for the localization of receptors, particularly MCH receptors, in tissue sections.

The invention provides compounds and compositions that are useful as inhibitors of MCH binding to MCH 1 receptor, and as inhibitors of MCH mediated signal transduction (e.g., they may be used as standards in assays of MCH binding and MCH-mediated signal transduction). The invention additionally comprises methods of inhibiting MCH binding to MCH receptors in vivo, preferably MCH 1 receptors present in the hypothalamus.

Accordingly, a broad embodiment of the invention is directed to a compounds and pharmaceutically acceptable salts of Formula I:

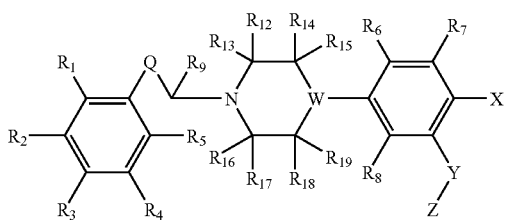

I wherein:
Q is a group of the Formula:

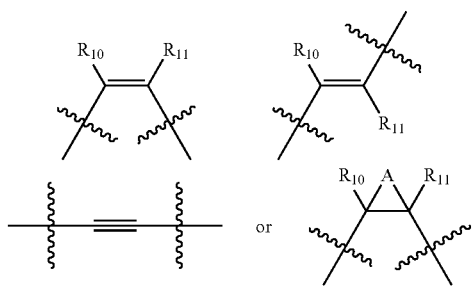

wherein
A is $C_1$-$C_5$ alkylene optionally mono-, di, or trisubstituted with substitutuents independently chosen from $C_1$-$C_3$ alkyl, $C_1$-$C_3$ alkoxy, halogen, halo($C_1$-$C_3$)alkyl, halo($C_1$-$C_3$)alkoxy, hydroxy, amino, and mono- or di($C_1$-$C_3$)alkylamino;

$R_1$, $R_2$, $R_3$, $R_4$, $R_5$, $R_6$, $R_7$, and $R_8$ are the same or different and represent hydrogen, halogen, cyano, nitro, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, hydroxy, amino, mono or di($C_1$-$C_6$)alkyl amino, halo($C_1$-$C_6$)alkyl, halo($C_1$-$C_6$)alkoxy, $C_1$-$C_6$ alkanoyl, $C_1$-$C_6$ alkoxycarbonyl, —COOH, —SO$_2$NH$_2$, mono or dialkylsulfonamido, —C(O)NH$_2$, or mono or di($C_1$-$C_6$)alkylcarboxamido;

$R_9$, $R_{10}$, $R_{11}$, $R_{12}$, $R_{13}$, $R_{14}$, $R_{15}$, $R_{16}$, $R_{17}$, $R_{18}$, and $R_{19}$ independently represent hydrogen or $C_1$-$C_6$ alkyl;

W is nitrogen or C—$R_a$ where $R_a$ represents hydrogen, hydroxy, $C_1$-$C_6$ alkoxy, $C_1$-$C_6$ alkyl or cyano;

X represents halogen, cyano, nitro, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, hydroxy, amino, mono or di($C_1$-$C_6$)alkylamino, halo($C_1$-$C_6$)alkyl, halo($C_1$-$C_6$)alkoxy, $C_1$-$C_6$ alkanoyl, $C_1$-$C_6$ alkoxycarbonyl, —COOH, —CONH$_2$, mono- or di($C_1$-$C_6$)alkylcarboxamido, —SO$_2$NH$_2$, mono or di($C_1$-$C_6$) alkylsulfonamido; or X represents phenyl which may be optionally substituted by up to five substituents, which may be the same or different and are selected from the group consisting of hydrogen, halogen, cyano, nitro, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, hydroxy, amino, mono or di($C_1$-$C_6$)alkyl amino, halo($C_1$-$C_6$)alkyl, halo ($C_1$-$C_6$)alkoxy, $C_1$-$C_6$ alkanoyl, $C_1$-$C_6$ alkoxycarbonyl, —COOH, —CONH$_2$, mono- or di-($C_1$-$C_6$)alkylcarboxamido, —SO$_2$NH$_2$, and mono or di($C_1$-$C_6$)alkylsulfonamido;

Y is oxygen, sulfur, —S(O)—, or —SO$_2$—; and
Z is $C_1$-$C_6$ alkyl or mono, di or trifluoromethyl.

The invention also provides intermediates and methods useful for preparing the compounds of Formula I.

DETAILED DESCRIPTION OF THE INVENTION

The invention particularly includes compounds and salts of Formula I wherein Q is a ring and A is methylene optionally substituted with $C_1$-$C_2$ alkyl.

The invention is also specifically directed to compounds and salts of Formula I wherein W is nitrogen or CH and A is methylene. Preferred compounds and salts of this class are those wherein $R_{10}$, $R_{11}$, $R_{12}$, $R_{13}$, $R_{14}$, $R_{15}$, $R_{16}$, $R_{17}$, $R_{18}$, and $R_{19}$ are hydrogen. Other preferred compounds and salts of this class are those wherein $R_{10}$, $R_{11}$, $R_{12}$, $R_{13}$, $R_{14}$, $R_{15}$, $R_{16}$, $R_{17}$, $R_{18}$, and $R_{19}$ are hydrogen, X is halogen; Y is oxygen; and Z is $C_1$-$C_6$ alkyl. Also preferred are compounds and salts of Formula I wherein W is nitrogen or CH and A is methylene, $R_{10}$, $R_{11}$, $R_{12}$, $R_{13}$, $R_{14}$, $R_{15}$, $R_{16}$, $R_{17}$, $R_{18}$, and $R_{19}$ are hydrogen, $R_1$, $R_2$, $R_3$, $R_4$, $R_5$, $R_6$, $R_7$, and $R_8$ may be the same or different and represent hydrogen, halogen, $C_1$-$C_6$ alkyl, $C_1$-$C_6$ alkoxy, trifluoromethyl, or trifluoromethoxy; X is hydrogen, halogen, or phenyl, or most preferably X is halogen; Y is oxygen; and Z is $C_1$-$C_6$ alkyl.

Particularly provided by the invention are compounds of Formula II

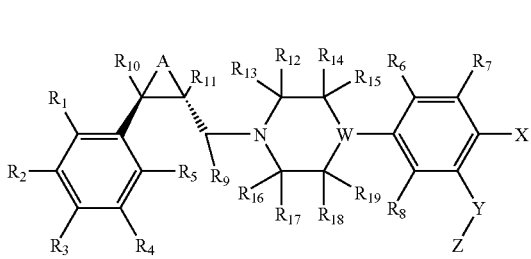

II and the pharmaceutically acceptable salts thereof; wherein

A is methylene optionally substituted with $C_1$-$C_2$ alkyl, and $R_1$-$R_{19}$, W, X, Y, and Z are as defined for Formula I.

Preferred compounds and salts of Formula II are those wherein W is nitrogen or CH.

Other preferred compounds and salts of Formula II are those wherein W is nitrogen or CH and $R_{10}$, $R_{11}$, $R_{12}$, $R_{13}$, $R_{15}$, $R_{17}$, $R_{18}$, and $R_{19}$ are hydrogen.

Also preferred are compounds and salts of Formula II wherein W is nitrogen or CH, $R_{10}$, $R_{11}$, $R_{12}$, $R_{13}$, $R_{15}$, $R_{17}$, $R_{18}$, and $R_{19}$ are hydrogen, $R_1$, $R_2$, $R_3$, $R_4$, $R_5$, $R_6$, $R_7$, and $R_8$ independently represent hydrogen, halogen, $C_1$-$C_6$ alkyl, $C_1$-$C_6$ alkoxy, trifluoromethyl, or trifluoromethoxy; $R_{14}$ and $R_{16}$ are the same or different and are either hydrogen or methyl; X is hydrogen, halogen, or phenyl; Y is oxygen; and Z is $C_1$-$C_6$ alkyl.

Particularly preferred compounds and salts of Formula II are those wherein W is nitrogen or CH, $R_1$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are hydrogen, $R_2$, $R_3$, $R_4$, and $R_5$ are independently hydrogen, $C_1$-$C_2$ alkyl, $C_1$-$C_2$ alkoxy, or halogen; X is halogen; Y is oxygen; and Z is $C_1$-$C_6$ alkyl.

The invention further provides compounds of Formula III

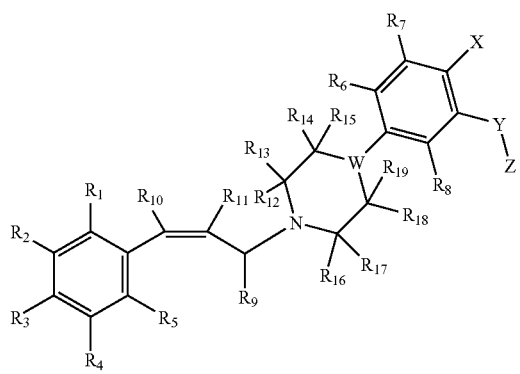

and the pharmaceutically acceptable salts thereof, wherein $R_1$-$R_{19}$, W, X, Y, and Z are as defined for Formula I.

Preferred compounds and salts of Formula III are those wherein $R_{13}$, $R_{15}$, $R_{17}$, $R_{19}$, are hydrogen; and $R_{10}$, $R_{11}$, $R_{12}$, $R_{14}$, $R_{16}$, and $R_{18}$ independently represent hydrogen or methyl, or more preferably hydrogen.

Also preferred are compounds and salts of Formula III, wherein $R_{10}$-$R_{19}$ are hydrogen, and W is N or CH.

More preferred compounds and salts of Formula III are those wherein $R_{10}$-$R_{19}$ are hydrogen, W is N or CH; $R_1$, $R_2$, $R_3$, $R_4$, $R_5$, $R_6$, $R_7$, and $R_8$ independently represent hydrogen, halogen, $C_1$-$C_6$ alkyl, $C_1$-$C_6$ alkoxy, trifluoromethyl, or trifluoromethoxy; X is hydrogen or halogen; Y is oxygen; and Z is $C_1$-$C_6$ alkyl.

Particularly preferred compounds and salts of Formula III are those wherein $R_{10}$-$R_{19}$ are hydrogen, W is N or CH, $R_1$, $R_2$, $R_3$, $R_4$ independently represent hydrogen, halogen, $C_1$-$C_2$alkyl, or $C_1$-$C_2$ alkoxy; $R_5$, $R_6$, $R_7$, and $R_8$ are hydrogen; X is halogen; Y is oxygen; and Z is $C_1$-$C_6$ alkyl.

Another embodiment of the invention is directed to compounds and salts of Formula IV

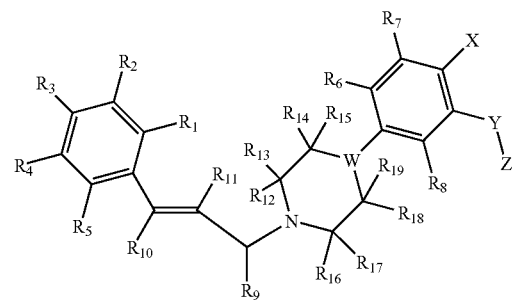

and the pharmaceutically acceptable salts thereof, wherein $R_1$-$R_{19}$, W, X, Y, and Z are as defined for Formula I.

Preferred compounds and salts of Formula IV are those wherein $R_{13}$, $R_{15}$, $R_{17}$, $R_{19}$, are hydrogen; and $R_{10}$, $R_{11}$, $R_{12}$, $R_{14}$, $R_{16}$, and $R_{18}$ independently represent hydrogen or methyl, or more preferably hydrogen.

Also preferred are compounds and salts of Formula IV, wherein $R_{10}$-$R_{19}$ are hydrogen, and W is N or CH.

More preferred compounds and salts of Formula IV are those wherein $R_{10}$-$R_{19}$ are hydrogen, W is N or CH; $R_1$, $R_2$, $R_3$, $R_4$, $R_5$, $R_6$, $R_7$, and $R_8$ independently represent hydrogen, halogen, $C_1$-$C_6$ alkyl, $C_1$-$C_6$ alkoxy, trifluoromethyl, or trifluoromethoxy; X is hydrogen or halogen; Y is oxygen; and Z is $C_1$-$C_6$ alkyl.

Particularly preferred compounds and salts of Formula IV are those wherein $R_{10}$-$R_{19}$ are hydrogen, W is N or CH, $R_1$, $R_2$, $R_3$, $R_4$ independently represent hydrogen, halogen, $C_1$-$C_2$alkyl, or $C_1$-$C_2$ alkoxy; $R_5$, $R_6$, $R_7$, and $R_8$ are hydrogen; X is halogen; Y is oxygen; and Z is $C_1$-$C_6$ alkyl.

The invention also provides compounds of Formula V

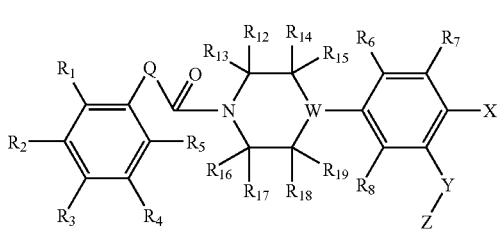

or a pharmaceutically acceptable salt thereof wherein:

Q is a group of the Formula:

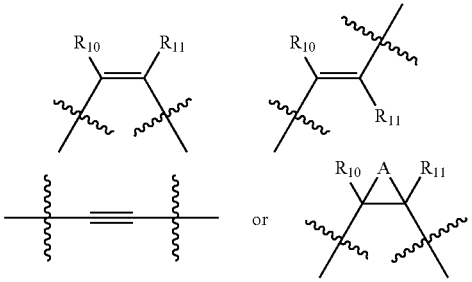

wherein:

A is $C_1$-$C_5$ alkylene optionally mono-, di, or trisubstituted with substitutuents independently chosen from $C_1$-$C_3$ alkyl, $C_1$-$C_3$ alkoxy, halogen, halo($C_1$-$C_3$)alkyl, halo($C_1$-$C_3$)alkoxy, hydroxy, amino, and mono- or di($C_1$-$C_3$)alkylamino;

$R_1$, $R_2$, $R_3$, $R_4$, $R_5$, $R_6$, $R_7$, and $R_8$ are the same or different and represent hydrogen, halogen, cyano, nitro, $C_1$-$C_6$ alkyl, $C_2$-$C_6$ alkenyl, $C_2$-$C_6$ alkynyl, $C_1$-$C_6$alkoxy, $C_1$-$C_6$ alkylthio, hydroxy, amino, mono or di($C_1$-$C_6$)alkyl amino, halo($C_1$-$C_6$)alkyl, halo($C_1$-$C_6$)alkoxy, $C_1$-$C_6$ alkanoyl, $C_1$-$C_6$ alkoxycarbonyl, —COOH, —$SO_2NH_2$, mono or dialkylsulfonamido, —C(O)$NH_2$, or mono or di($C_1$-$C_6$)alkylcarboxamido;

$R_{10}$, $R_{11}$, $R_{12}$, $R_{13}$, $R_{14}$, $R_{15}$, $R_{16}$, $R_{17}$, $R_{18}$, and $R_{19}$ independently represent hydrogen or $C_1$-$C_6$ alkyl;

W is nitrogen or C—$R_a$ where $R_a$ represents hydrogen, hydroxy, $C_1$-$C_6$ alkoxy, $C_1$-$C_6$ alkyl or cyano;

X represents halogen, cyano, nitro, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, hydroxy, amino, mono or di($C_1$-$C_6$)alkylamino, halo($C_1$-$C_6$)alkyl, halo($C_1$-$C_6$)alkoxy, $C_1$-$C_6$ alkanoyl, $C_1$-$C_6$ alkoxycarbonyl, —COOH, —CONH$_2$, mono- or di($C_1$-$C_6$)alkylcarboxamido, —SO$_2$NH$_2$, mono or di($C_1$-$C_6$) alkylsulfonamido; or X represents phenyl which may be optionally substituted by up to five substituents, which may be the same or different and are selected from the group consisting of hydrogen, halogen, cyano, nitro, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, hydroxy, amino, mono or di($C_1$-$C_6$)alkyl amino, halo($C_1$-$C_6$)alkyl, halo($C_1$-$C_6$)alkoxy, $C_1$-$C_6$ alkanoyl, $C_1$-$C_6$ alkoxycarbonyl, —COOH, —CONH$_2$, mono- or di-($C_1$-$C_6$)alkylcarboxamido, —SO$_2$NH$_2$, and mono or di($C_1$-$C_6$)alkylsulfonamido;

Y is oxygen, sulfur, —S(O)—, or —SO$_2$—; and

Z is $C_1$-$C_6$ alkyl or mono, di or trifluoromethyl.

Compounds of Formula V are intermediates, useful in preparing compounds MCH 1 receptor ligands.

Preferred compounds of Formula V are those wherein Q is a group the formula

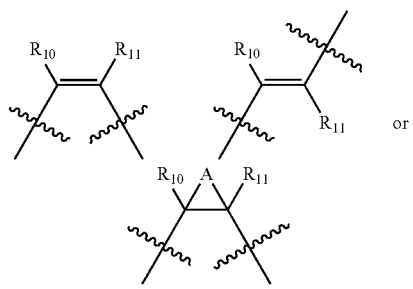

where A is methylene optionally substituted with $C_1$-$C_2$ alkyl or A is a single bond. Such compounds will be referred to as compounds of Formula VA.

The invention is particularly directed to compounds of Formula VA wherein W is nitrogen or CH.

More preferred compounds of Formula VA are those wherein W is nitrogen or CH, and $R_{10}$, $R_{11}$, $R_{12}$, $R_{13}$, $R_{14}$, $R_{15}$, $R_{16}$, $R_{17}$, $R_{18}$, and $R_{19}$ are hydrogen.

Other preferred compounds of Formula VA are those wherein W is nitrogen or CH, $R_{10}$, $R_{11}$, $R_{12}$, $R_{13}$, $R_{14}$, $R_{15}$, $R_{16}$, $R_{17}$, $R_{18}$, and $R_{19}$ are hydrogen, X is halogen; Y is oxygen; and Z is $C_1$-$C_6$ alkyl.

Especially preferred compounds of Formula VA are those wherein W is nitrogen or CH, $R_{10}$, $R_{11}$, $R_{12}$, $R_{13}$, $R_{14}$, $R_{15}$, $R_{16}$, $R_{17}$, $R_{18}$, and $R_{19}$ are hydrogen, $R_1$, $R_2$, $R_3$, $R_4$, $R_5$, $R_6$, $R_7$, and $R_8$ may be the same or different and represent hydrogen, halogen, $C_1$-$C_6$ alkyl, $C_1$-$C_6$ alkoxy, trifluoromethyl, or trifluoromethoxy; X is halogen; Y is oxygen; and Z is $C_1$-$C_6$ alkyl.

Particularly preferred compounds of Formula V include those where Q is a group of the formula:

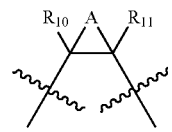

where A is methylene optionally substituted with $C_1$-$C_2$ alkyl. These compounds are hereinafter referred to as compounds of Formula VI-A. Specific compounds of Formula VI-A include those where A is methylene and $R_{10}$ and $R_{11}$ are methyl or, preferably, hydrogen.

Specific compounds of VA include those wherein W is nitrogen or CH. Preferred compounds of V and VA include those wherein $R_{10}$, $R_{11}$, $R_{12}$, $R_{13}$, $R_{14}$, $R_{15}$, $R_{16}$, $R_{17}$, $R_{18}$, and $R_{19}$ are hydrogen.

Other specific compounds of VA include those wherein: X is halogen; Y is oxygen; and Z is $C_1$-$C_6$ alkyl.

Still other specific compounds of VA include those where $R_1$, $R_2$, $R_3$, $R_4$, $R_5$, $R_6$, $R_7$, and $R_8$ are the same or different and represent hydrogen, halogen, $C_1$-$C_6$ alkyl, $C_1$-$C_6$ alkoxy, trifluoromethyl, or trifluoromethoxy;

X is halogen;

Y is oxygen; and

Z is $C_1$-$C_6$ alkyl.

Preferably not more than 5, and more preferably not more than 3, cyano or nitro groups are present in compounds of Formula I-Formula VA. Preferably not more than 2 of $R_1$, $R_2$, $R_3$, $R_4$, $R_5$ are non-hydrogen substituents. Preferably not more than 5 and more preferably not more than 3 of $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are non-hydrogen substituents.

Representative compounds of Formula I are shown in Table 1.

TABLE 1

| Compound number | Chemical Structure |
|---|---|
| 1 | 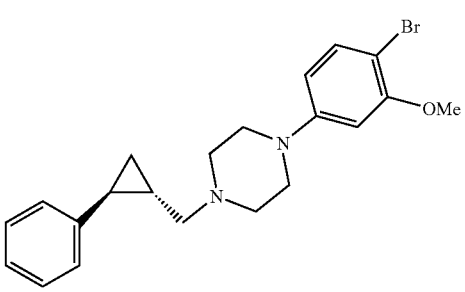 |

TABLE 1-continued

| Compound number | Chemical Structure |
|---|---|
| 2 | 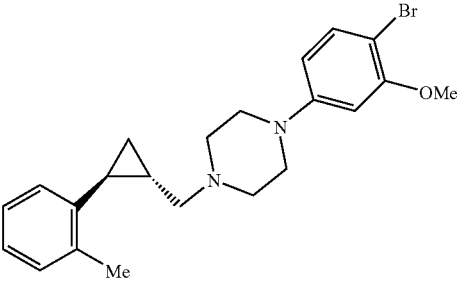 |
| 3 | 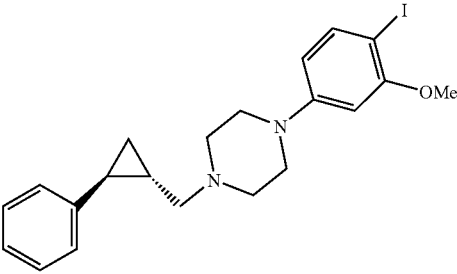 |
| 4 | 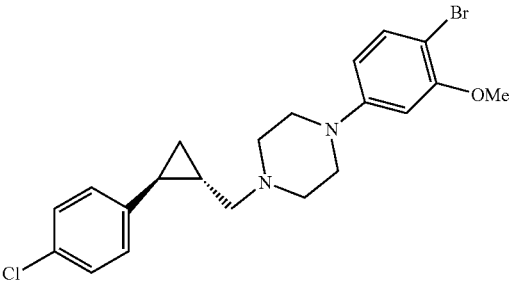 |
| 5 | 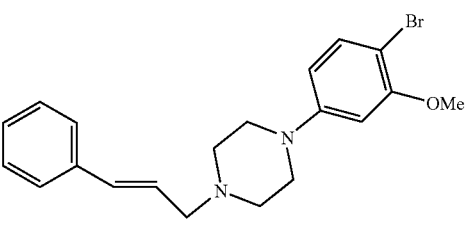 |
| 6 | 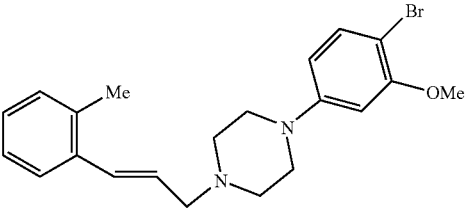 |

In certain situations, the compounds of this invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Asymmetric synthesis of compounds of the invention may be performed using the methods illustrated in Example 1, below. For compounds having an alpha-methyl benzyl group ($R_3$ is methyl, $R_4$ is hydrogen) the R enantiomer is preferred. Resolution of the racemates can be accomplished, for example, by conventional methods such as crystallization in the presence of a resolving agent, or chromatography, using, for example a chiral HPLC column.

Representative compounds of the invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Those skilled in the art will recognize a wide variety of non-toxic pharmaceutically acceptable addition salts.

The invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautormers. The invention includes all tautomeric forms of a compound.

This invention relates to compounds that bind with high affinity to the melanin concentrating hormone receptors, including human melanin concentrating hormone receptors. This invention also includes such compounds that bind with high selectivity to the melanin concentrating hormone receptors, including human and monkey melanin concentrating hormone receptors. Without wishing to be bound to any particular theory, it is believed that the interaction of the compounds of Formula I with the melanin concentrating hormone receptor results in the pharmaceutical utility of these compounds.

The invention further comprises methods of treating patients in need of such treatment with an amount of a compound of the invention sufficient to alter the symptoms of a disorder.

The diseases and/or disorders that can also be treated using compounds and compositions according to the invention include, but are not limited to, eating disorders, sexual disorders, obesity, bulimia, anorexia, diabetes, heart disease, stroke, anorgasmia, or psychogenic impotence.

The invention also provides pharmaceutical compositions comprising at least one compound of the invention together with at least one pharmaceutically acceptable carrier or excipient. Such pharmaceutical compositions include packaged pharmaceutical compositions for treating disorders responsive to melanin concentrating hormone receptor modulation, e.g., treatment of eating disorders such as obesity or bulimia or treatment of sexual disorders such as anorgasmic or psychogenic impotence. The packaged pharmaceutical compositions include a container holding a therapeutically effective amount of at least one melanin concentrating hormone receptor modulator as described supra and instructions (e.g., labeling) indicating that the contained composition is to be used for treating a disorder responsive to melanin concentrating hormone receptor modulation in the patient.

The invention also pertains to methods of inhibiting the binding of melanin concentrating hormone to melanin concentrating hormone receptors which methods involve contacting a compound of the invention with cells expressing melanin concentrating hormone receptors, wherein the compound is present at a concentration sufficient to inhibit melanin concentrating hormone binding to melanin concentrating hormone receptors in vitro. This method includes inhibiting the binding of melanin concentrating hormone to melanin concentrating hormone receptors in vivo, e.g., in a patient given an amount of a compound of Formula I that would be sufficient to inhibit the binding of melanin concentrating hormone to melanin concentrating hormone receptors in vitro. The amount of a compound that would be sufficient to inhibit the binding of melanin concentrating hormone to the melanin concentrating hormone receptor in vitro may be readily determined via a melanin concentrating hormone receptor binding assay, such as the assay described in Example 5. The membranes, comprising melanin concentrating hormone receptors, used to determine in vitro binding may be obtained from a variety of sources, for example from preparations of HEK 293 cells expressing cloned human or cloned monkey melanin concentrating hormone receptors, especially HEK 293 cells expressing such receptors.

The invention also pertains to methods for altering the signal-transducing activity of MCH receptors, particularly the MCH receptor-mediated release of intracellular calcium, said method comprising exposing cells expressing such receptors to an effective amount of a compound of the invention. This method includes altering the signal-transducing activity of MCH receptors in vivo, e.g., in a patient given an amount of a compound of Formula I that would be sufficient to alter the signal-transducing activity of MCH receptors in vitro. The amount of a compound that would be sufficient to alter the signal-transducing activity of MCH receptors may be determined via a MCH receptor signal transduction assay, such as the calcium mobilization assay described in Example 6.

The melanin concentrating hormone receptor ligands provided by this invention and labeled derivatives thereof are also useful as standards and reagents in determining the ability of a potential pharmaceutical to bind to the melanin concentrating hormone receptor.

Labeled derivatives the melanin concentrating hormone receptor ligands provided by this invention are also useful as radiotracers for positron emission tomography (PET) imaging or for single photon emission computerized tomography (SPECT).

Preferred compounds of the invention do not exhibit fungicidal activity. Such a lack of fungicidal activity may be demonstrated by no more than a 40% reduction of colony size (when treated with the compound at 100 p.p.m. and compared to untreated controls) of *Aspergillus nidulans* strain R153 when grown for 48 hours at 32° C. on solid MAG medium. Optionally, BENOMYL, 100 p.p.m., may be used as a positive control. MAG medium is 2% malt extract, 0.2% peptone, 1% glucose and trace elements, pH 6.5. Trace elements as a 5000-fold concentrate consist of 10 g/l EDTA, 4.4 g/l $ZnSO_4.7H_2O$, 1.01 g/l $MnCl_2.4H_2O$, 0.32 g/l $CoCl_2.6H_2O$, 0.315 g/l $CuSO_4.5H_2O$, 0.22 g/l $(NH_4)_6Mo_7O_{24}.H_2O$, 1.47 g/l $CaCl_2.2H_2O$ and 1.0 g/l $FeSO_4.7H_2O$. Medium is made solid by the addition of 1.5% agar.

Alternatively, such a lack of fungicidal activity may be demonstrated by an infection frequency of 60-100% (as compared to untreated plants) for each of *Puccinia recondita* (leaf rust) on wheat, *Erysiphe graminis* (powdery mildew)

on barley, *Venturia inaequalis* (scab, black spot) on apple plants, and *Cercospora arachidicola* (early leafspot) on peanut.

The technique employed to determine fungicidal activity is as follows. The plants are grown in John Innes Potting Compost (No. 1, or Seed, as appropriate) in 4 cm diameter mini-pots. A layer of fine sand is placed at the bottom of the pot to facilitate uptake of test compound by the roots.

The test compounds are formulated, e.g., by bead-milling with aqueous Dispersol T or as a solution in acetone/ethanol which is diluted to the required concentration immediately before use. 100 p.p.m. a.i. suspensions are sprayed on to the foilage and applied to the roots of the same plant via the soil. (Sprays are applied to maximum retention, and root drenches to a final concentration equivalent to approximately 40 ppm a.i./dry soil). Tween 20, to give a final concentration of 0.1%, is added when the sprays are applied to the cereals.

For most of the tests, the test compound is applied to the soil (roots) and to the foliage (by spraying) one or two days before the plant is inoculated with the diseases. An exception is the test on *Erysiphe graminis*, in which the plants are inoculated 24 hours before treatment. After inoculation, the plants are put into an appropriate environment to allow infection to take place and then incubated until the disease is ready for assessment. The period between inoculation and assessment typically varies from 4 to 14 days according to the disease and environment.

Chemical Description and Terminology

The compounds of the invention have asymmetric centers; this invention includes all of the optical isomers and mixtures thereof.

Compounds of the invention with carbon-carbon double bonds occur in Z- and E- forms; all isomeric forms of the compounds are included in the invention.

When any variable occurs more than one time in Formula I, its definition on each occurrence is independent of its definition at every other occurrence.

By "$C_1$-$C_6$ alkyl" or in the invention is meant straight or branched chain alkyl groups or cycloalkyl groups having 1-6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$-C6 alkyl groups are methyl, ethyl, propyl, butyl, cyclopropyl, cyclopropylmethyl, cyclohexyl, cycloheptyl, norbornyl, and the like. Particularly preferred alkyl groups are methyl and ethyl.

By "$C_1$-$C_6$ alkoxy" in the invention is meant an alkyl group of indicated number of carbon atoms attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. Preferred alkoxy groups herein are $C_1$-$C_4$ alkoxy groups. Particularly preferred alkoxy groups are ethoxy and methoxy.

The term "halogen" includes fluorine, chlorine, bromine, and iodine. Where X is halogen in Formula I-Formula V, bromine is particularly preferred.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups are trifluoromethyl and difluoromethyl. Preferably not more than 5, and more preferably not more than 3 haloalkyl groups, are present in compounds of the invention.

"Haloalkoxy" represents a haloalkyl group as defined above with the indicated number of carbon atoms attached through an oxygen bridge.

Non-toxic "pharmaceutically acceptable salts" include, but are not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium. The invention also encompasses the prodrugs of the compounds of Formula I.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have desirable pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120-1127).

Compounds of Formula I exhibit good activity in standard in vitro MCH receptor binding assays and/or calcium mobilization assays, specifically in the assays as specified in Examples 5 and 6, which follow. References herein to "standard in vitro receptor binding assay" are intended to refer to that protocol as defined in Example 5 which follows. References herein to "standard MCH 1 receptor calcium mobilization assay" are intended to refer to that protocol as defined in Example 6 which follows. Generally, preferred compounds of Formula I have an $K_i$ of about 1 micromolar or less, still more preferably a $K_i$ of about 100 nanomolar or less even more preferably a $K_i$ of about 10 nanomolar or less or even 1 nanomolar or less in such a defined standard in vitro MCH 1 receptor binding assay and exemplied by Example 5. Generally preferred compounds of Formula I are MCH 1 receptor antagonists and exhibit $EC_{50}$ values of about 4 micromolar or less, more preferably 1 micromolar or less, still more preferably $EC_{50}$ values of about 100 nanomolar or less even more preferably an $EC_{50}$ value of about 10 nanomolar or less or even 1 nanomolar or less in such a defined standard in vitro MCH 1 receptor mediated calcium mobilization assay as exemplified by Example 6 which follows.

Preferred compounds of Formula I do not interact with dopamine receptors, particularly human dopamine D2 and D4 receptors. Dopamine receptor binding assays may be preformed using the methods described in Example 9 which follows. Preferred compounds of Formula I exhibit $K_i$ values greater than 1 micromolar in standard assays of dopamine receptor binding assays such as the dopamine D2 and D4 receptor binding assays described in Example 9.

EXAMPLES

Preparation of Compounds

The compounds of the invention can be prepared essentially according to the synthetic procedure shown in Scheme 1. As shown, a 2-phenylacylcycloalkyl compound of general structure 7 may be condensed with a 4-arylpiperazine or piperidine of general structure 8 in the presence of a reducing agent to provide a compound of general Formula I. The reducing agent may be sodium borohydride, sodium triacetoxy borohydride, lithium aluminum hydride, alane or the like. Alternatively, an acid chloride or an acid can be coupled with the piperazine to generate an amide which can in turn be reduced to yield the desired compound of Formula I.

The preparation of a specific compound of this invention (the 1S,2S enantiomer of Compound 1) is described graphically in Scheme 2 and the synthetic steps used are presented within Example 1. Within Scheme 2, 1S,2S 2-phenylcyclopropanecarboxylic acid (9) was condensed with 1-(4-bromo-3-methoxyphenyl)piperazine (10) in the presence of 1-(3-dimethylaminopropyl)-3-ethylcarbodiimide (EDCI), dimethylaminopyridine (DMAP) and 1-hydroxybenzotriazole (HOBT). The resulting amide 11 was reduced to the desired amine by reduction with alane in tetrahydrofuran.

Those having skill in the art will recognize that the starting materials may be varied and additional steps employed to produce compounds encompassed by the invention, as demonstrated by the following examples. Unless otherwise specified all reagents and solvent are of standard commercial grade and are used without further purification.

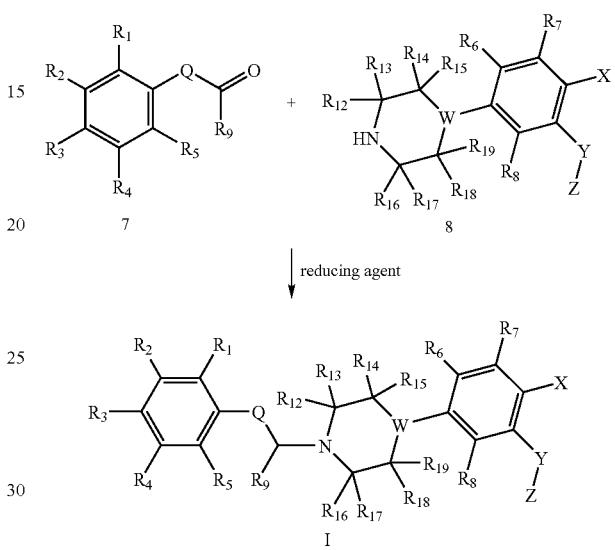

Scheme 1

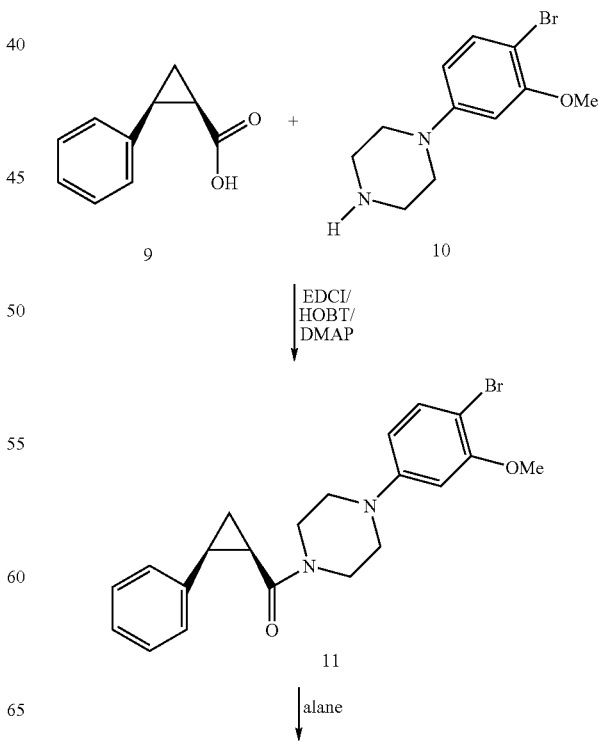

Scheme 2
Preparation of 1S, 2S Enantiomer of Compound I

-continued

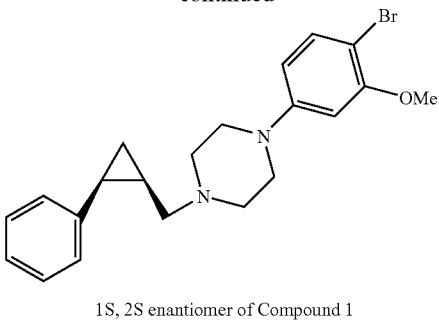

1S, 2S enantiomer of Compound 1

Example 1

Preparation of (1S, 2S)-1-(4-bromo-3-methoxyphenyl)-4-(trans-2-phenylcyclopropyl)methylpiperazine.

Compound numbers 9-11 in the following example represent compounds shown in Scheme 2.

1-(4-Bromo-3-methoxyphenyl)piperazine (10)

A solution of 1-(3-methoxyphenyl)piperazine dihydrobromide (3.5 g, 10 mmol) is dissolved in DMSO (30 mL) and heated at 65° C. for 4 h in a flask which is open to the atmosphere. After cooling, the mixture is poured into a separatory funnel containing 100 mL of 1 N sodium hydroxide solution and extracted with ethyl ether (3×100 mL). The organic extracts are dried ($Na_2SO_4$), filtered, and concentrated to provide 1-(4-bromo-3-methoxyphenyl)piperazine as a solid. $^1$H NMR (400 MHz, $CDCl_3$) 7.34-7.36 (d, J=2.2 Hz, 1H,), 6.47 (s, 1H), 6.38-6.41 (d, J=2.8 Hz, 1H), 3.87 (s, 3H, OMe), 3.11-3.13 (m, 4H), 3.01-3.03 (m, 4H)

(1S,2S)-1-(4-bromo-3-methoxyphenyl)-4-(trans-2-phenylcyclopropyl) carbonylpiperazine (11).

EDCI (0.42 g, 2.2 mmol), DMAP (0.27 g, 2.2 mmol) and HOBT (0.23 g, 2.2 mmol) are added to a solution of acid 9 (0.34 g, 2.1 mmol) and piperazine 10 (0.54 g, 2.0 mmol) in chloroform (15 mL) and the resulting solution allowed to stir overnight. The solution is washed with water (10 mL), saturated $NaHCO_3$ solution, (10 mL), brine (10 mL) and dried over magnesium sulfate. After filtration the solution is concentrated and the resulting oil purified by column chromatography eluting with 2% methanol in chloroform to provide the desired amide 11 as a white sticky solid. $^1$H NMR (400 MHz, $CDCl_3$) 7.1-7.5 (m, 6H), 6.50 (s, 1H), 6.40 (d, J=7 Hz, 1H), 3.89 (s, 3H, OMe), 3.8 (bm, 4H), 3.2 (bm, 4H), 2.5 (m, 1H), 1.98 (m, 1H), 1.70 (m, 1H), 1.35 (m, 1H), LCMS (CI) 416 (M+1).

(1S, 2S)-1-(4-bromo-3-methoxyphenyl)-4-(trans-2-phenylcyclopropyl) methylpiperazine (Compound 1, Table 1)

A solution of alane triethylamine complex (3.13 mL, 1.57 mmol) is added to a solution of amide 11 (0.65 g, 1.57 mmol) in THF (10 mL) at 0° C. After 45 min, the reaction is quenched with water and extracted with ether. The organic extracts are dried ($MgSO_4$), filtered, and concentrated to a colorless oil which is purified by column chromatography eluting with 5% MeOH/chloroform to provide the desired compound 1 as a colorless oil. $^1$H NMR (400 MHz, $CDCl_3$) 7.38 (d, J=7 Hz, 1H), 7.1-7.35 (m, 5H,), 6.45 (d, J=1 Hz, 1H), 6.40 dd, J=7, 1 Hz, 1H), 3.88 (s, 3H, OMe), 3.2 (m, 4H), 2.7 (m, 4H), 2.63 (m, 1H), 2.40 (dd, J=12,5 Hz, 1H), 1.70 (m, 1H), 1.25 (m, 1H), 0.85-1.0 (m, 2H).

Example 2

The following compounds are prepared essentially according to the procedures described with respect to Schemes 1 and 2 and further set forth in Example 1. Variations suitable for preparing the following compounds will be readily apparent to those skilled in the art of organic synthesis:

a) 1-(4-Bromo-3-methoxyphenyl)-4-(trans-2-phenylcyclopropyl) methylpiperazine
b) 1R, 2R-1-(4-Bromo-3-methoxyphenyl)-4-(trans-2-phenylcyclopropyl) methylpiperazine
c) 1-(4-Iodo-3-methoxyphenyl)-4-(trans-2-phenylcyclopropyl) methylpiperazine
d) 1-(4-Chloro-3-methoxyphenyl)-4-(trans-2-phenylcyclopropyl) methylpiperazine
e) 1-(4-Phenyl-3-methoxyphenyl)-4-(trans-2-phenylcyclopropyl) methylpiperazine
f) 1-(4-Bromo-3-methoxyphenyl)-4-[trans-2-(3-methoxyphenyl)cyclopropyl]methylpiperazine
g) 1-(4-Bromo-3-methoxyphenyl)-4-(trans-2-[4-chlorophenyl]cyclopropyl) methylpiperazine (compound 4)
h) 1-(4-Bromo-3-methoxyphenyl)-4-(trans-2-[2-methylphenyl]cyclopropyl)methylpiperazine (compound 2)
i) 1-(4-Bromo-3-methoxyphenyl)-4-(trans-2-[4-methoxyphenyl]cyclopropyl)methylpiperazine
j) 1-(4-Bromo-3-methoxyphenyl)-4-([3-phenyl]propen-2-yl)piperazine (Compound 5)
k) 1-(4-Bromo-3-methoxyphenyl)-4-([3-{2-methylphenyl}]propen-2-yl)piperazine (compound 6)
l) 1-(3-Methoxyphenyl)-4-([3-phenyl]propen-2-yl)piperazine
m) 1-(4-Bromo-3-methoxyphenyl)-4-([3-{3-methylphenyl}]propen-2-yl)piperazine
n) 1-(4-Bromo-3-methoxyphenyl)-4-([3-{2-methoxyphenyl}]propen-2-yl)piperazine
o) 1-(4-Bromo-3-methoxyphenyl)-4-([3-{3-chlorophenyl}]propen-2-yl)piperazine
p) 1-(4-Bromo-3-methoxyphenyl)-4-([3-{3-ethoxyphenyl}]propen-2-yl)piperazine
q) 1-(4-Bromo-3-methoxyphenyl)-4-([3-{2,3-dimethoxyphenyl}]propen-2-yl)piperazine
r) 1-(4-Bromo-3-methoxyphenyl)-4-([3-{3,4-dimethoxyphenyl}]propen-2-yl)piperazine
s) 1-(4-Bromo-3-methoxyphenyl)-4-([3-{2,5-dimethoxyphenyl}]propen-2-yl)piperazine
t) 1-(4-Bromo-3-methoxyphenyl)-4-([3-{2,4-dimethoxyphenyl}]propen-2-yl)piperazine
u) 1-(4-Bromo-3-methoxyphenyl)-4-(trans-2-phenylcyclopropyl) methylpiperidine
v) 1-(4-Iodo-3-methoxyphenyl)-4-(trans-2-phenylcyclopropyl) methylpiperidine
w) 1-(4-Chloro-3-methoxyphenyl)-4-(trans-2-phenylcyclopropyl) methylpiperidine
x) 1-(4-Methyl-3-methoxyphenyl)-4-(trans-2-phenylcyclopropyl) methylpiperidine
y) 1-(4-Trifluormethyl-3-methoxyphenyl)-4-(trans-2-phenylcyclopropyl) methylpiperidine
z) 1-(4-Bromo-3-ethoxyphenyl)-4-(trans-2-phenylcyclopropyl) methylpiperidine.

Example 3

Cells expressing MCH 1 Receptors

Cells or preparations of cells recombinantly expressing human MCH 1 receptors, monkey MCH 1 receptors, or chimeric human MCH 1/human Beta 2 Adrenergic receptors may be used in the radioligand binding assay and Calcium Mobilization assay which follows. The preparation of expression vectors for such MCH 1 Receptors has been described previously, e.g. in U.S. Provisional Application No. 60/216,081, filed Jul. 6, 2000 and U.S. Provisional Application 60/284,835, filed Apr. 19, 2001, pages 19-20 and the sequence listing, both of which application are hereby incorporated by reference for their teachings regarding the cloning and expression of MCH 1 receptors.

Preparation of HEK 293 Cells Expressing the Monkey MCH Receptor

HEK 293 cells are stably transfected via standard calcium phosphate precipitation procedures with a Cynamolgus macaque monkey MCH expression vector described previously or other MCH 1 receptor expression vector.

Cells are grown to confluency at 37 C, 5% $CO_2$, approximately 48-72 hours, in DMEM high glucose culture medium (catalog #10-017-CV, MEDIATECH, Herndon, Va.) supplemented with 10% fetal bovine serum, 25 mM HEPES, and 500 ug/ml G418 The cells are pelleted by gentle centrifugation. Cell pellets are washed twice with cold PBS, harvested in cold PBS containing 5 mM EDTA, and stored at −80 C.

Preparation of CHO Cells Expressing the Monkey MCH Receptor

CHO (Chinese Hamster Ovary) cells are transfected via standard calcium phosphate precipitation procedures with an MCH 1 receptor expression vector.

Cells are grown to confluency at 37 C, 5% $CO_2$, approximately 48-72 hours, in Ham's F12 culture medium (catalog #10-080-CV, MEDIATECH, Herndon, Va.) supplemented with 10% fetal bovine serum, 25 mM HEPES, and 500 ug/ml (active) G418. The cells are pelleted by gentle centrifugation. Cell pellets are washed twice with cold PBS, harvested in cold PBS containing 5 mM EDTA, and stored at −80° C.

Example 4

Purified Membranes

HEK 293 cell pellets stored frozen at −80° C. are thawed by addition of wash buffer (25 mM Hepes with 1.0 mM $CaCl_2$, 5.0 mM $MgCl_2$, 120 mM NaCl, PH7.4) and homogenized for 30 seconds using a BRINKMAN POLYTRON, setting 5. Cells are centrifuged for 10 minutes at 48,000×g. The supernatant is discarded and the pellet is resuspended in fresh wash buffer, and homogenized again. The protein concentration of the resulting membrane preparation is measured using the Bradford protein assay (Bio-Rad Laboratories, Hercules, Calif.). By this measure, a 1-liter culture of cells typically yields 50-75 mg of total membrane protein.

Example 5

Radioligand Binding Assays for Modulators of Chimeric Receptors

Purified membranes from HEK 293 cells expressing the monkey MCH receptor are prepared by the procedure given in Example 3. The membrane homogenate is centrifuged as before and resuspended to a protein concentration of 333 ug/ml in binding buffer (Wash buffer+0.1% BSA and 1.0 uM final conc. phosphoramidon) for an assay volume of 50 ug membrane protein/150 ul binding buffer. Phosphoramidon is from SIGMA BIOCHEMICALs, St. Louis, Mo. (cat# R-7385).

Competition binding assays are performed at room temperature in Falcon 96 well round bottom polypropylene plates. To each assay well is added: 150 ul of MCH receptor containing membranes in binding buffer, prepared as described above, 50 ul $^{125}$I-Tyr MCH in binding buffer, 50 ul binding buffer, and 2 ul test compound in DMSO. $^{125}$I-Tyr MCH (specific activity=2200 Ci/mMol) is purchased from NEN, Boston, Mass. (Cat # NEX 373) and is diluted in binding buffer to provide a final assay concentration of 30 pM.

Non-specific binding is defined as the binding measured in the presence of 1 uM unlabeled MCH. MCH is purchased from BACHEM U.S.A., King of Prussia, Pa. (cat # H-1482). To each assay well used to determine non-specific MCH binding is added: 150 ul of MCH receptor-containing membranes in binding buffer, 50 ul $^{125}$I-Tyr MCH in binding buffer, unlabeled MCH in 25 ul binding buffer, and 25 ul binding buffer.

Assay plates are incubated for 1 hour at room temperature. Membranes are harvested onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

For saturation binding the concentration of $^{125}$I-Tyr MCH is varied from 7-1,000 pM. Typically 11 concentration points are collected per saturation binding curve.

Equilibrium binding parameters are determined by fitting the allosteric Hill equation to the measured values with the aid of the computer program FitP™ (BIOSOFT, Ferguson, Mo.).

Example 6.

Functional Assay of Monkey MCH Receptors

Calcium Mobilization Assay

The following assay can be used to monitor the response of cells expressing melanin concentrating hormone receptors to melanin concentrating hormone. The assay can also be used to determine if test compounds act as agonists or antagonists of melanin concentrating hormone receptors.

Chinese Hamster Ovary (CHO) cells stably transfected with an MCH 1 receptor expression vector are grown to a density of 15,000 cells/well in FALCON black-walled, clear-bottomed 96-well plates (#3904, BECTON-DICKINSON, Franklin Lakes, N.J.). Prior to running the assay the culture medium is emptied from the 96 well plates. Fluo-3 calcium sensitive dye (Molecular Probes, Eugene, Oreg.) is added to each well (dye solution: 1 mg FLUO-3 AM, 440 uL DMSO and 440 ul 20% pluronic acid in DMSO, diluted 1:4, 50 ul diluted solution per well). Plates are covered with aluminum foil and incubated at 37° C. for 1-2 hours. After the incubation the dye solution is emptied from the plates, cells are washed once in 100 ul KRH buffer (0.05 mM KCl, 0.115 M NaCl, 9.6 mM $NaH_2PO_4$, 0.01 mM $MgSO_4$, 25 mM HEPES, pH 7.4) to remove excess dye; after washing 80 ul KRH buffer is added to each well.

Determination of Agonist Effects

Fluorescence response may monitored upon the addition of either human MCH or test compound as described below by a FLIPR™ plate reader (Molecular Devices, Sunnyvale, Calif.) by excitation at 480 nM and emission at 530 nM.

Determination of Antagonist Effects

In order to measure the ability of a test compound to antagonize the response of cells expressing MCH receptors to MCH, the $EC_{50}$ of MCH is first determined.

An additional 20 ul of KRH buffer and 1 ul DMSO is added to each well of cells, prepared as described immediately above. 100 ul human MCH in KRH buffer is automatically transferred by the FLIPR instrument to each well. An 8-point concentration response curve, with final MCH concentrations of 1 nM to 3 uM, is used to determine MCH $EC_{50}$.

Test compounds are dissolved in DMSO, diluted in 20 ul KRH buffer, and added to cells prepared as described above. The 96 well plates containing prepared cells and test compounds are incubated in the dark, at room temperature for 0.5-6 hours. It is important that the incubation not continue beyond 6 hours. Just prior to determining the fluorescence response 100 ul human MCH diluted in KRH buffer to $2 \times EC_{50}$ is automatically added by the FLIPR instrument to each well of the 96 well plate for a final sample volume of 200 ul and a final MCH concentration of $EC_{50}$. The final concentration of test compounds in the assay wells is between 1 uM and 5 uM. Typically cells exposed to one $EC_{50}$ of MCH exhibit a fluorescence response of about 10,000 Relative Fluorescence Units. Antagonists of the MCH receptor exhibit a response that is significantly less than that of the control cells to the $p \leq 0.05$ level, as measured using a parametric test of statistical significance. Typically antagonists of the MCH receptor decrease the fluorescence response relative to control cells by about 20%, preferably by about 50%, and most preferably by at least 80% as compared to matched controls.

Determination of Agonist Effects

The ability of a compound to act as an agonist of the MCH receptor may be determined by measuring the fluorescence response of cells expressing MCH receptors, using the methods described above, in the absence of MCH. Compounds that cause cells to exhibit fluorescence above background are MCH 1 receptor agonists.

Example 7

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Example 8

Use of Compounds of the Invention as Probes for Melanin Receptors in Cultured Cells and Tissue Samples Receptor autoradiography (receptor mapping) of melanin concentrating hormone receptors in cultured cells or tissue samples is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 9

Determination of $D_2$ and $D_4$ Receptor Binding Activity

The following assay is a standard assay for determining the binding affinity of compounds to dopamine $D_4$ and $D_2$ receptors.

Pellets of Chinese hamster ovary (CHO) cells containing recombinantly expressing primate $D_2$, human $D_4$ dopamine receptors are used for the assays. The sample is homogenized in 100 volumes (w/vol) of 0.05 M Tris HCl buffer containing 120 mM NaCl, 5 mM $MgCl_2$ and 1 mM EDTA at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM $^{3}H$-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding is defined as that binding found in the presence of 1 micromolar spiperone; without further additions, nonspecific binding is less than 20% of total binding.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A packaged pharmaceutical composition comprising:
   (a) a pharmaceutical composition comprising:
      (i) a compound of the formula:

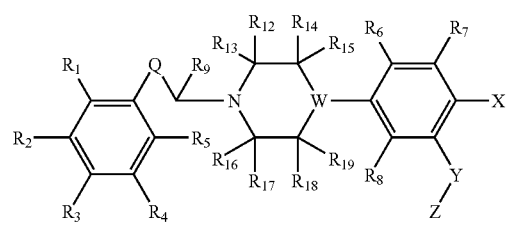

or a pharmaceutically acceptable salt thereof wherein:
Q represents a group of the Formula:

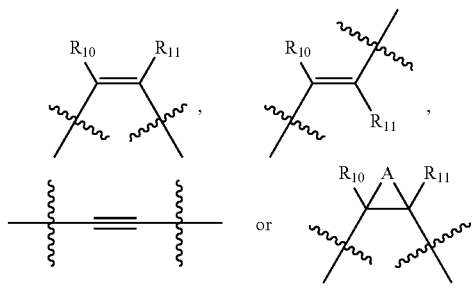

wherein A is C$_1$-C$_5$ alkylene optionally mono-, di, or trisubstituted with substituents independently chosen from C$_1$-C$_3$ alkyl, C$_1$-C$_3$ alkoxy, halogen, halo(C$_1$-C$_3$)alkyl, halo(C$_1$-C$_3$)alkoxy, hydroxy, amino, and mono- or di(C$_1$-C$_3$) alkylamino;

R$_1$, R$_2$, R$_3$, R$_4$, R$_5$, $_6$, R$_7$, and R$_8$ are the same or different and independently represent hydrogen, halogen, cyano, nitro, C$_1$-C$_6$ alkyl, C$_2$-C$_6$ alkenyl, C$_2$-C$_6$ alkynyl, C$_1$-C$_6$ alkoxy, C$_1$-C$_6$ alkylthio, hydroxy, amino, mono or di(C$_1$-C$_6$) alkyl amino, halo(C$_1$-C$_6$)alkyl, halo(C$_1$-C$_6$)alkoxy, C$_1$-C$_6$ alkanoyl, C$_1$-C$_6$ alkoxycarbonyl, —COOH, —SO$_2$NH$_2$, mono or dialkylsulfonamido, —C(O)NH$_2$, or mono or di(C$_1$-C$_6$)alkylcarboxamido;

R$_9$, R$_{10}$, R$_{11}$, R$_{12}$, R$_{13}$, R$_{14}$, R$_{15}$, R$_{16}$, R$_{17}$, R$_{18}$, and R$_{19}$ independently represent hydrogen or $_1$-C$_6$ alkyl;

W is nitrogen or C—R$_a$ where R$_a$ represents hydrogen, hydroxy, C$_1$-C$_6$ alkoxy, C$_1$-C$_6$ alkyl or cyano;

X represents halogen, cyano, nitro, C$_1$-C$_6$ alkyl, C$_2$-C$_6$ alkenyl, C$_2$-C$_6$ alkynyl, C$_1$-C$_6$ alkoxy, C$_1$-C$_6$ alkylthio, hydroxy, amino, mono or di(C$_1$-C$_6$)alkylamino, halo(C$_1$-C$_6$)alkyl, halo(C$_1$-C$_6$)alkoxy, C$_1$-C$_6$ alkanoyl, C$_1$-C$_6$ alkoxycarbonyl, —COOH, —CONH$_2$, mono- or di(C$_1$-C$_6$)alkylcarboxamido, —SO$_2$NH$_2$, mono or di(C$_1$-C$_6$)alkylsulfonamido; or X represents phenyl which may be optionally substituted by up to five substituents, which may be the same or different and are selected from the group consisting of hydrogen, halogen, cyano, nitro, C$_1$-C$_6$ alkyl, C$_2$-C$_6$ alkenyl, C$_2$-C$_6$ alkynyl, C$_1$-C$_6$ alkoxy, C$_1$-C$_6$ alkylthio, hydroxy, amino, mono or di(C$_1$-C$_6$) alkyl amino, halo(C$_1$-C$_6$)alkyl, halo(C$_1$-C$_6$)alkoxy, C$_1$-C$_6$ alkanoyl, C$_1$-C$_6$ alkoxycarbonyl, —COOH, —CONH$_2$, mono- or di-(C$_1$-C$_6$) alkylcarboxamido, —SO$_2$NH$_2$ and mono or di(C$_1$-C$_6$)alkylsulfonamido;

Y is oxygen, sulfur, —S(O)—, or —SO$_2$-; and

Z is C$_1$-C$_6$ alkyl or mono, di or trifluoromethyl; and (ii) at least one pharmaceutically acceptable carrier or excipient; and (b) instructions for using the composition to treat a patient suffering from obesity.

2. A packaged pharmaceutical composition according to claim 1, wherein the instructions are provided as labeling and the package includes a container holding the compound or the pharmaceutically acceptable salt thereof and the at least one pharmaceutically acceptable carrier or excipient.

3. A packaged pharmaceutical composition according to claim 1, wherein Q is a group of the Formula:

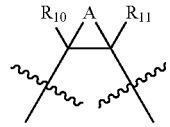

and A is methylene optionally substituted with C$_1$-C$_2$ alkyl.

4. A packaged pharmaceutical composition according to claim 3, wherein A is methylene and W is nitrogen.

5. A packaged pharmaceutical composition according to claim 4, wherein R$_{10}$, R$_{11}$, R$_{12}$, R$_{13}$, R$_{14}$, R$_{15}$, R$_{18}$, R$_{17}$, R$_{18}$ and R$_{19}$ are hydrogen.

6. A packaged pharmaceutical composition according to claim 5 wherein:

R$_1$, R$_2$, R$_3$, R$_5$, R$_6$, R$_7$ and R$_8$ are independently hydrogen, halogen, C$_1$-C$_6$alkyl, C$_1$-C$_6$ alkoxy, trifluoromethyl or trifluoromethoxy;

X is halogen or phenyl;

Y is oxygen; and

Z is C$_1$-C$_6$ alkyl.

7. A packaged pharmaceutical composition according to claim 3, wherein A is methylene and W is CH.

8. A packaged pharmaceutical composition according to claim 7, wherein R$_{10}$, R$_{11}$, R$_{12}$, R$_{13}$, R$_{14}$, R$_{15}$, R$_{16}$, R$_{17}$, R$_{18}$ and R$_{19}$ are hydrogen.

9. A packaged pharmaceutical composition according to claim 8, wherein:

R$_1$, R$_2$, R$_3$, R$_4$, R$_5$, R$_5$, R$_7$ and R$_8$ are independently hydrogen, halogen, C$_1$-C$_6$ alkyl, C$_1$-C$_6$ alkoxy, trifluoromethyl or trifluoromethoxy;

X is halogen or phenyl;

Y is oxygen; and

Z is C$_1$-C$_6$ alkyl.

10. A packaged pharmaceutical composition according to claim 1, wherein the compound has the formula:

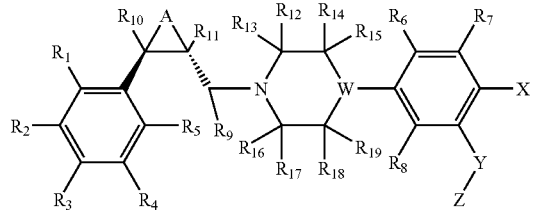

wherein A is methylene optionally substituted with C$_1$-C$_2$ alkyl.

11. A packaged pharmaceutical composition according to claim 1, wherein the compound has the formula:

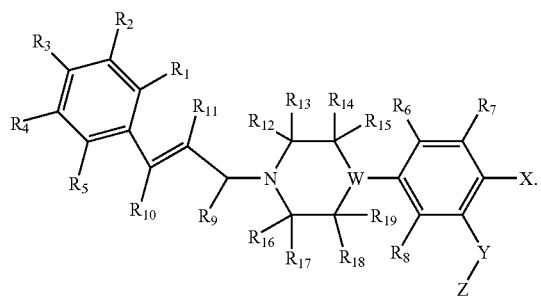

12. A packaged pharmaceutical composition according to claim 11, wherein

R$_{13}$, R$_{15}$, R$_{17}$ and R$_{19}$ are hydrogen;

R$_{10}$, R$_{11}$, R$_{12}$, R$_{14}$, R$_{16}$ and R$_{18}$ independently represent hydrogen or methyl;

W is N or OH;

R$_1$, R$_2$, R$_3$, R$_4$, R$_5$, R$_6$, R$_7$, and R$_6$ independently represent hydrogen, halogen, C$_1$C$_6$ alkyl, C$_1$-C$_6$ alkoxy, trifluoromethyl or trifluoromethoxy;

X is hydrogen or halogen;

Y is oxygen; and

Z is C$_1$-C$_6$ alkyl.

13. A packaged pharmaceutical composition according to claim 1 wherein the compound has the formula:

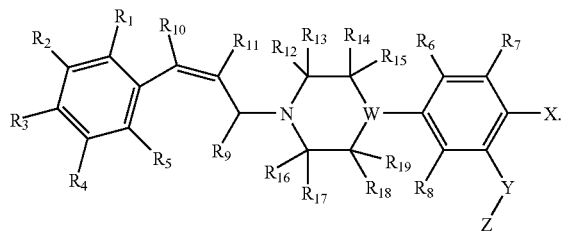

14. A packaged pharmaceutical composition according to claim 13, wherein

R$_{13}$, R$_{15}$, R$_{17}$ and R$_{19}$ are hydrogen;

R$_{10}$, R$_{11}$, R$_{12}$, R$_4$, R$_{16}$ and R$_{18}$ independently represent hydrogen or methyl;

W is N or CH;

R$_1$, R$_2$, R$_3$R$_4$, R$_5$, R$_6$, R$_7$, and R$_8$ independently represent hydrogen, halogen; C$_1$-C$_6$ alkyl, C$_1$-C$_6$ alkoxy, trifluoromethyl or trifluoromethoxy;

X is hydrogen or halogen;

Y is oxygen; and

Z is C$_1$-C$_6$ alkyl.

15. A packaged pharmaceutical composition according to claim 1, wherein the compound is selected from:

1-(4-Bromo-3-methoxyphenyl)-4-(trans-2-phenylcyclopropyl) methylpiperazine;

(1S, 2S)-1-(4-bromo-3-methoxyphenyl)-4-(trans-2-phenylcyclopropyl)methylpiperazine;

1R, 2R-1-(4-Bromo-3-methoxyphenyl)-4-(trans-2-phenylcyclopropyl) methylpiperazine;

1-(4-Iodo-3-methoxyphenyl)-4-(trans-2-phenylcyclopropyl) methylpiperazine;

1-(4-Chloro-3-methoxyphenyl)-4-(trans-2-phenylcyclopropyl) methylpiperazine;

1-(4-Phenyl-3-methoxyphenyl)-4-(trans-2-phenylcyclopropyl) methylpiperazine;

1-(4-Bromo-3-methoxyphenyl)-4-[trans-2-(3-methoxyphenyl)cyclopropyl] methylpiperazine;

1-(4-Bromo-3-methoxyphenyl)-4-(trans-2-[4-chlorophenyl] cyclopropyl) methylpiperazine;

1-(4-Bromo-3-methoxyphenyl)-4-(trans-2-[2-methylphenyl] cyclopropyl)methylpiperazine;

1-(4-Bromo-3-methoxyphenyl)-4-(trans-2-[4-methoxyphenyl] cyclopropyl) methylpiperazine;

1-(4-Bromo-3-methoxyphenyl)-4-(trans-2-phenylcyclopropyl) methylpiperidine;

1-(4-Iodo-3-methoxyphenyl)-4-(trans-2-phenylcyclopropyl) methylpiperidine;

1-(4-Chloro-3-methoxyphenyl)-4-(trans-2-phenylcyclopropyl) methylpiperidine;

1-(4-Methyl-3-methoxyphenyl)-4-(trans-2-phenylcyclopropyl) methylpiperidine;

1-(4-Trifluormethyl-3-methoxyphenyl)-4-(trans-2-phenylcyclopropyl) methylpiperidine;

1-(4-Bromo-3-ethoxyphenyl)-4-(trans-2-phenylcyclopropyl) methylpiperidine;

1-(4-Bromo-3-methoxyphenyl)-4-([3-phenyl]propen-2-yl)piperazine;

1-(4-Bromo-3-methoxyphenyl)-4-([3-{2-methylphenyl}] propen-2-yl)piperazine;

1-(3-Methoxyphenyl)-4-([3-phenyl]propen-2-yl)piperazine;

1-(4-Bromo-3-methoxyphenyl)-4-([3-{3-methylphenyl}] propen-2-yl)piperazine;

1-(4-Bromo-3-methoxyphenyl)-4-([3-{2-methoxyphenyl}]propen-2-yl)piperazine;

1-(4-Bromo-3-methoxyphenyl)-4-([3-{3-chlorophenyl}] propen-2-yl)piperazine;

1-(4-Bromo-3-methoxyphenyl)-4-([3-{3-ethoxyphenyl}] propen-2-yl)piperazine;

1-(4-Bromo-3-methoxyphenyl)-4-([3-{2,3-dimethoxyphenyl}]propen-2-yl)piperazine;

1-(4-Bromo-3-methoxyphenyl)-4-([3-{3,4-dimethoxyphenyl}]propen-2-yl)piperazine;

1-(4-Bromo-3-methoxyphenyl)-4-([3-{2,5-dimethoxyphenyl}]propen-2-yl)piperazine; and 1-(4-Bromo-3-methoxyphenyl)-4-([3-{2,4-dimethoxyphenyl}]propen-2-yl)piperazine.

* * * * *